(12) United States Patent
Genereux et al.

(10) Patent No.: US 9,694,154 B2
(45) Date of Patent: Jul. 4, 2017

(54) SOUND MACHINE WITH PSEUDO RANDOM WHITE NOISE GENERATOR

(71) Applicant: HEADWATERS, INC., Marblehead, MA (US)

(72) Inventors: Philippe J. Genereux, Ottawa (CA); Rudy A. Vandenbelt, Ottawa (CA)

(73) Assignee: Headwaters Inc, Marblehead, MA (US)

( * ) Notice: Subject to any disclaimer, the term of this patent is extended or adjusted under 35 U.S.C. 154(b) by 44 days.

(21) Appl. No.: 13/796,581

(22) Filed: Mar. 12, 2013

(65) Prior Publication Data

US 2014/0249359 A1    Sep. 4, 2014

Related U.S. Application Data

(60) Provisional application No. 61/771,656, filed on Mar. 1, 2013.

(51) Int. Cl.
*A61M 21/02* (2006.01)
*H04R 25/00* (2006.01)
*A61M 21/00* (2006.01)

(52) U.S. Cl.
CPC ............ *A61M 21/02* (2013.01); *H04R 25/75* (2013.01); *A61M 2021/0027* (2013.01)

(58) Field of Classification Search
CPC ....... H04R 25/75; H03M 3/332; A61M 21/02; A61M 2021/0027

USPC .......................................... 600/28
See application file for complete search history.

(56) References Cited

U.S. PATENT DOCUMENTS

2009/0163828 A1     6/2009  Turner
2009/0208030 A1*    8/2009  Anderson et al. ........... 381/73.1
2012/0283593 A1    11/2012  Searchfield

OTHER PUBLICATIONS

Anderson et al. "Pseudo-Random and Random Test Signals" Hewlett-Packard Journal, 19(1), pp. 1-20 (1967).*

* cited by examiner

*Primary Examiner* — Christine H Matthews
*Assistant Examiner* — Kaylee Wilson
(74) *Attorney, Agent, or Firm* — Albert Peter Durigon

(57) ABSTRACT

A sound machine having a pseudo random white noise generator provides white noise sound therapy of selectable tone/texture, bandwidth and/or peak frequency to those suffering from tinnitus or others seeking noise-masking or sleep or relaxation. The sound machine having a pseudo random white noise generator includes a user input interface having a tone/texture user input control, a band pass user input control and a peak select user input control. The tone/texture user input control selects the tone/texture of the white noise sound generated, the bandpass user input control the bandpass of the white noise sound generated and the peak select user input control provides the ability to select frequency peaks of the white noise sound generated.

6 Claims, 6 Drawing Sheets

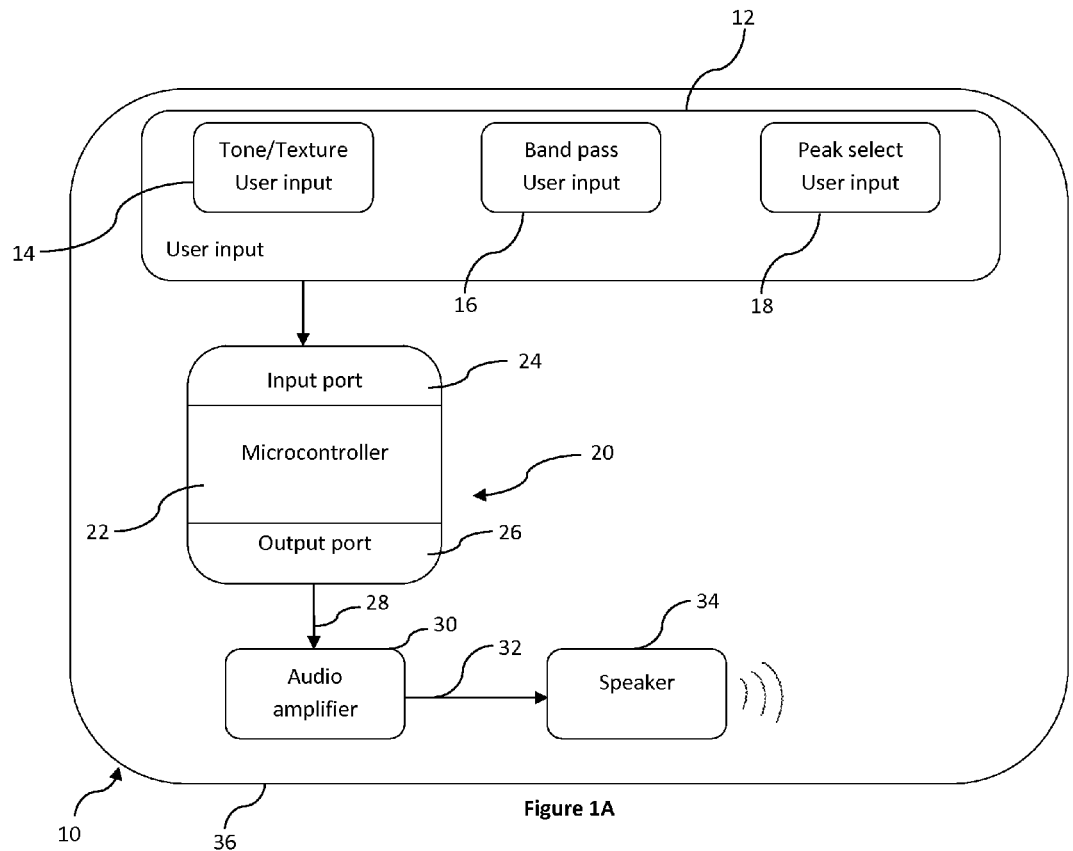
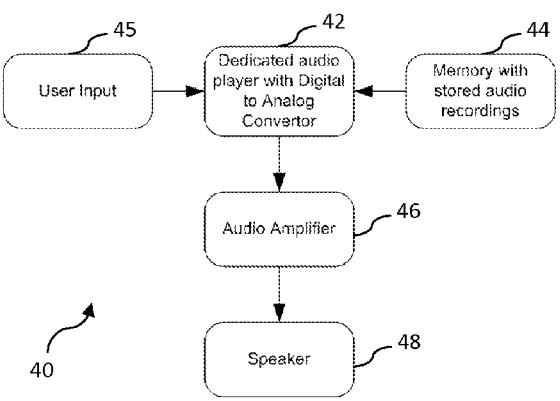
Figure 1A
Figure 1B (Prior Art)

| Cycle | Function | Register | Value |
|---|---|---|---|
| Initialize | | Seed 1 | 01001111 |
| | | Seed 2 | 10111111 |
| | | Seed 3 | 10111111 |
| | | Divisor | 00011010 |
| 1 | RLF | Seed 1 | 10011110 |
| | | Seed 2 | 01111110 |
| | | Seed 3 | 01111111 |
| | | CARRY | 1 |
| | XOR | Divisor | 00011010 |
| | | Seed 1 | 10000100 |
| | | CARRY | 1 |
| | | Output | 1 |
| 2 | RLF | Seed 1 | 00001000 |
| | | Seed 2 | 11111101 |
| | | Seed 3 | 11111110 |
| | | CARRY | 0 |
| | Skip XOR | Divisor | 00011010 |
| | | Seed 1 | 00001000 |
| | | CARRY | 0 |
| | | Output | 0 |
| 3 | RLF | Seed 1 | 00010000 |
| | | Seed 2 | 11111010 |
| | | Seed 3 | 11111101 |
| | | CARRY | 1 |
| | XOR | Divisor | 00011010 |
| | | Seed 1 | 00001010 |
| | | CARRY | 1 |
| | | Output | 1 |
| 4 | RLF | Seed 1 | 00011100 |
| | | Seed 2 | 11101000 |
| | | Seed 3 | 11110111 |
| | | CARRY | 1 |
| | XOR | Divisor | 00011010 |
| | | Seed 1 | 00000110 |
| | | CARRY | 1 |
| | | Output | 1 |

SOUND MACHINE WITH PSEUDO RANDOM WHITE NOISE GENERATOR

CROSS-REFERENCE TO RELATED APPLICATIONS

This invention claims the benefit of U.S. provisional application Ser. No. 61/771,656, filed 1 Mar. 2013, of the same inventive entity as herein, incorporated herein by reference.

FIELD OF THE INVENTION

This invention is drawn to the field of audio components, and more particularly, to a novel sound machine having a pseudo random white noise generator providing white noise sound therapy to those suffering from tinittus or others seeking noise-masking or sleep or relaxation therapy.

BACKGROUND OF THE INVENTION

White noise sounds are known to reduce suffering from tinnitus and to provide noise-masking. When listened to during the day, they mask noise, and may help to reduce suffering from tinnitus, and at night they may help to mask noise and to fall asleep.

However, not all white noise sounds provide relief and noise masking equally to all tinnitus sufferers and to others who may benefit from white noise sound therapy.

For example, white noise sounds with different bandwidth are known to benefit different types of tinnitus sufferers. Some people benefit from white noise sounds having bandwidths providing more emphasis on higher frequency components whereas others benefit more from white noise sounds having bandwidths providing emphasis on lower frequency components.

It may also be desirable to have white noise sounds with different tones. Some listeners may find some tones more beneficial than others.

Others may suffer from ringing in the ears at particular frequencies. White noise sounds with different embedded peak frequencies matched to the ringing in the ears are known to help to block the ringing and thereby to bring some modicum of relief to the tinnitus sufferer.

The sound machines heretofore typically included a dedicated micro controller for sound playback and a memory having prerecorded therein one or more of these different types of white noise sounds to provide different sleep therapy regimens to tinnitus sufferers and others who may benefit from white noise sound therapy.

However, the utility of the heretofore known sound machines was limited by their comparatively-high component costs. Not only were dedicated micro controllers for sound playback comparatively-expensive, but the greater the number and variety of sounds stored in memory, the greater was the cost for each increment of additional memory capacity, with the result that the heretofore known sound machines could cost more than some tinnitus sufferers and others who may have benefitted from white noise therapy could practicably afford.

Accordingly, there is a need to provide a sound machine providing sound therapy for tinnitus sufferers and others seeking white noise sound therapy having the benefits of the heretofore known sound machines but none of their attendant disadvantages.

SUMMARY OF THE INVENTION

Accordingly, it is a principal object of the present invention to disclose a sound machine having a pseudo random white noise generator providing sound therapy to those suffering from tinnitus or others seeking noise-masking or sleep or relaxation therapy.

Another object of the present invention is to disclose a sound machine having a pseudo random white noise generator providing white noise sound therapy of different tone, bandwidth and/or peak frequency to those suffering from tinnitus or others seeking noise-masking or sleep or relaxation without the need for and memory cost of the heretofore known sound machines thereby extending the benefits of white noise sound therapy to a broader and more inclusive group of consumers.

In accord with these and other objects, the sound machine with pseudo random noise generator providing sound therapy of the present invention includes a user interface. A pseudo random white noise generator is disclosed that includes a processor and input and output ports. The input port of the processor of the pseudo random white noise generator is coupled to the user interface. The processor of the pseudo random noise generator is operative in response to user input control information to provide a pseudo random digital bit stream at its output port at a bit rate suitable for sound therapy. An analog amplifier is coupled to the output port and responsive to the pseudo random digital bit stream at a bit rate suitable for sound therapy to provide an analog white noise signal at a frequency audible to tinnitus sufferers and others seeking noise-masking or help to relax or to fall asleep. A speaker is coupled to the amplifier and is responsive to the analog white noise signal to provide white noise sound therapy.

The user interface may include a user tone control input coupled to the input port of the processor. The processor of the pseudo random white noise generator is operative to controllably change the bit rate of the pseudo random bit stream and thereby the tone/texture of the analog signal in response to user tone control input.

The user interface may include a user bandpass control input coupled to the input port of the processor. The processor of the pseudo random white noise generator is operative to controllably change the sequence of the "1's" and "0's" of the pseudo random bit stream and thereby the bandwidth of the analog signal in response to user bandpass control input.

The user interface may include a user peak frequency control input coupled to the input port of the processor. The processor of the pseudo random white noise generator is operative to controllably change the sequence of the "1's" and "0's" of the pseudo random bit stream and thereby one or more peak frequencies of the analog signal in response to user peak frequency control input.

One or more different peak frequencies may be provided by one or more comparatively-narrow bandpass filters.

BRIEF DESCRIPTION OF THE DRAWINGS

These and other objects, inventive aspects and advantageous features of the present invention will become apparent as the invention becomes better understood by referring to the following solely exemplary detailed description of the presently preferred embodiments, and to the drawings, wherein:

FIG. 1A is a block diagram illustrating the sound machine having a pseudo random white noise generator of the present invention;

FIG. 1B is a block diagram of a prior art sound machine;

DETAILED DESCRIPTION OF THE PRESENTLY PREFERRED EMBODIMENTS

Figure 2:
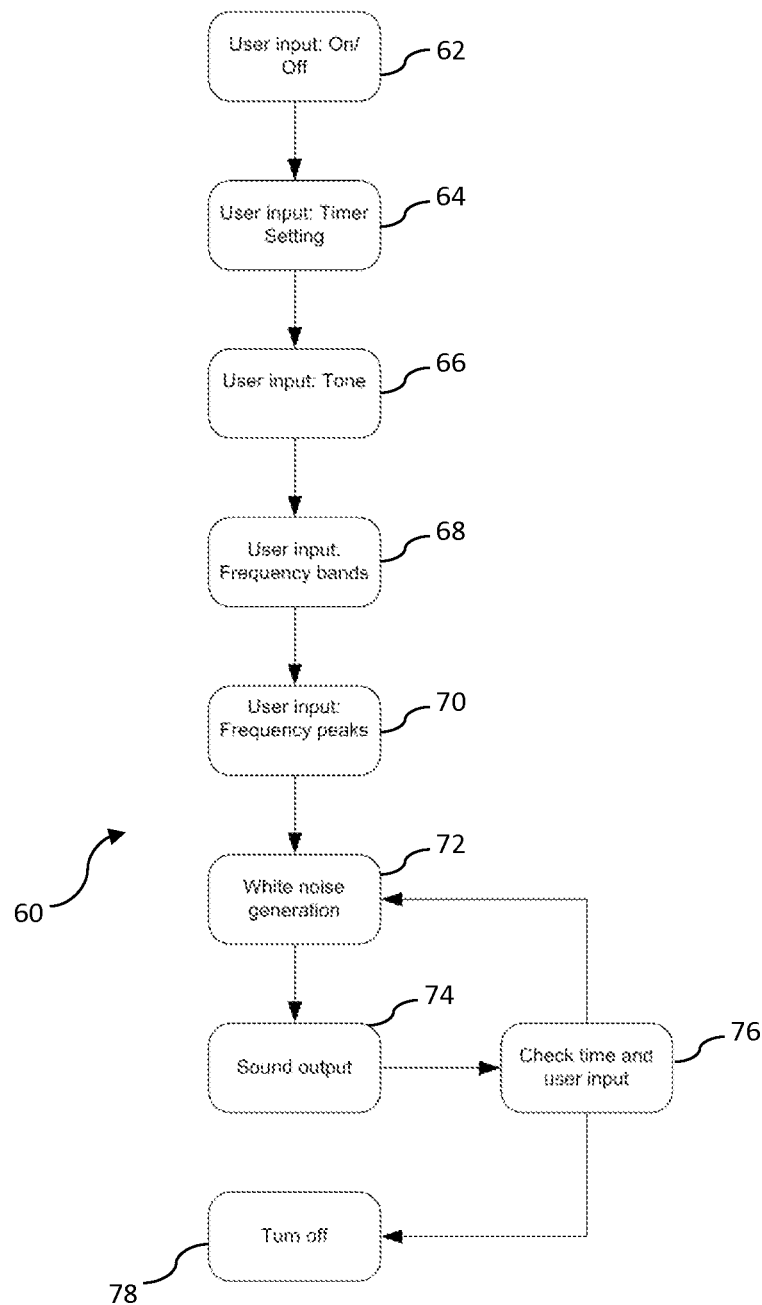
FIG. 2 is a flowchart illustrating the operation of the sound machine of the present invention having a pseudo random white noise generator.

Referring now to FIG. 1A, generally designated at 10 is a block diagram of a sound machine having a pseudo random white noise generator in accord with the present invention. The sound machine 10 includes a housing, not shown, a user input interface 12 having a tone/texture user input control 14, a band pass user input control 16 and a peak select user input control 18.

The tone/texture user input control 14 selects the tone/texture of the white noise sound generated, the bandpass user input control 16 the bandpass of the white noise sound generated and the peak select user input control 18 provides the ability to select frequency peaks of the white noise sound generated. User input control, not shown, is provided to set an auto on/off timer and to turn the sound machine 10 on/off. Any suitable user input device(s) known to those skilled in the art may be employed.

Sound machine 10 includes a pseudo random white noise generator generally designated 20 having a processor 22 and input and output ports 24, 26. The user input 14 is connected to the input port 24 of the processor 22 of the pseudo random white noise generator 20.

Any suitable microcontroller or other processor could be employed without departing from the inventive concepts.

The processor 22 is operative in response to user input control information to provide a pseudo random digital bit stream schematically illustrated by arrow 28 at its output port 26 at a bit rate suitable for sound therapy.

An audio amplifier 30 coupled to the output port 26 is operative in response to the pseudo random digital bit stream 28 at a bit rate suitable for sound therapy to provide an analog white noise signal schematically illustrated by arrow 32 at a frequency audible to tinnitus sufferers and others seeking noise-masking or help to relax or to fall asleep. No separate digital to analog converter is needed to produce the analog white noise signal 32.

A speaker 34 mounted to the housing and responsive to the analog white noise signal 32 provides white noise sound therapy to a listener, not shown, who may be using the sound machine to try to relax, mask noise, to fall asleep or otherwise to benefit from white noise sound therapy.

The sound machine 10 includes a housing schematically illustrated by box 36.

Referring now to FIG. 1B, generally designated at 40 is a block diagram illustrating a prior art sound machine. The sound machine 40 includes a dedicated audio player with digital/analog converter 42 coupled to memory 44 having prerecorded white noise sounds stored therein. The digital audio player 42 in response to user input via user input control 45 individually plays the white noise sounds stored in the memory 44. The analog output of the dedicated audio player with digital/analog converter 42 is amplified in audio amplifier 46 and played through the speaker 48. As will be readily appreciated, the prior art sound machine 40 is disadvantageous in that it includes comparatively-expensive dedicated audio players with digital to analog converters and comparatively-costly memory in which prerecorded white noise sounds are stored for individual replay thereby rendering these prior art sound machines comparatively-expensive and therewith limiting their utility to the narrower and less inclusive group of consumers able to afford them.

Referring now to FIG. 2, generally designated at 60 is a flowchart illustrating the operation of the sound machine of the present invention having a pseudo random white noise generator. When the sound machine is "on" as shown by the block 62, the processor is operative to determine whether the timer has been set as shown by block 64, whether a white noise sound with a particular tone/texture has been selected as shown by block 66, whether a white noise sound with a particular bandpass has been selected as shown by block 68, and whether a white noise sound with particular frequency peaks has been selected as shown by block 70.

As shown by the block 72, the processor is then operative to generate in response to the user input a pseudo random white noise bit stream at a bit rate suitable for white noise sound therapy having tone/texture, bandpass, and/or peak frequencies in accord with the user input selection(s). As shown by the blocks 72, 74, 76, 78, the processor is then operative to provide each pseudo random white noise sound selected for each selected timer duration.

Figure 3:
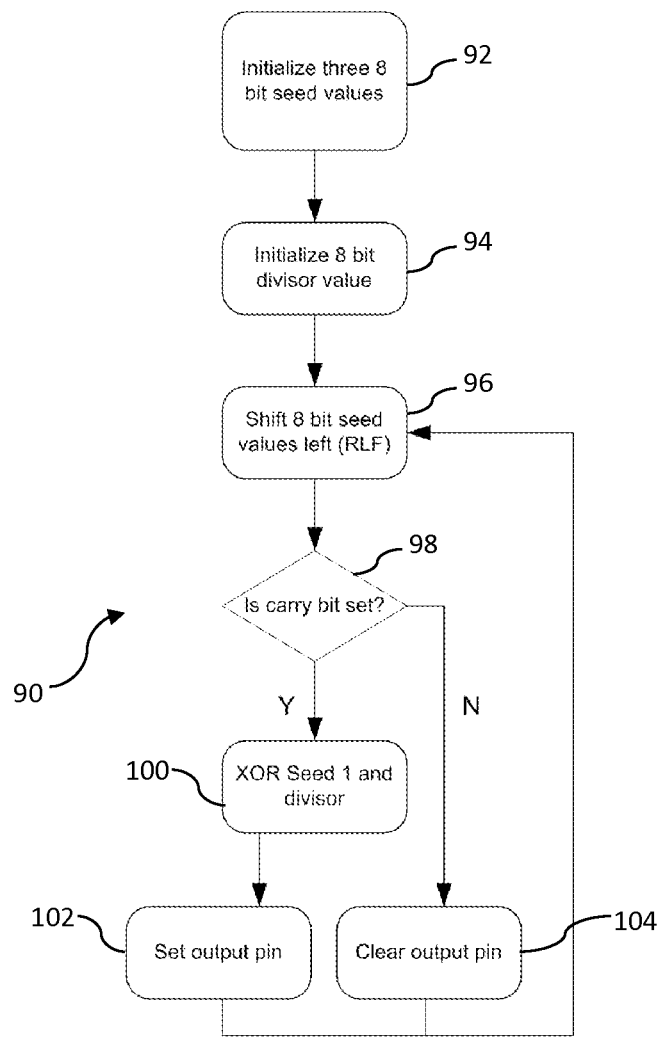
FIG. 3 is a flowchart illustrating the manner the processor of the pseudo random white noise generator algorithmically generates in real time a pseudo random bit stream at a bit rate suitable for sound therapy.

Referring now to FIG. 3, generally designated at 90 is a flowchart illustrating the manner the processor of the pseudo random white noise generator algorithmically generates in real time a pseudo random bit stream at a bit rate suitable for sound therapy.

As shown by the block 92, the algorithm begins with a twenty-five (25) bit number composed of three eight (8) bit numbers assigned to variables plus the micro controller's (processor's) STATUS register carry bit.

As shown by the block 94, an eight (8) bit divisor number is assigned to a constant.

As shown by the block 96, the bits in each eight (8) bit number are shifted left with the last bit overflowing into the carry register.

Following this operation, the CARRY bit is tested as shown by the block 98. If the value of the CARRY bit is set, an exclusive OR is performed between a constant (the value of the constant divisor) and the first of the three seeds as shown by block 100, the output port is set as shown by block 102 and processing returns to the block 96.

If the CARRY bit is not set, the exclusive OR is skipped, the output port is cleared as shown by block 104 and processing returns to block 96.

Example of Pseudo Random White Noise Generation Algorithm

Figures 4A, 4B:
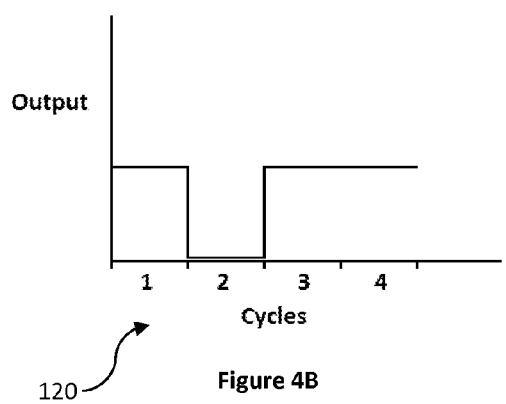
FIG. 4A is a table showing four cycles of one presently preferred pseudo random algorithm generating a pseudo random white noise bit stream and FIG. 4B is a graph of the bit stream output each cycle useful in explaining the operation of the pseudo random white noise generator.

Referring now to FIG. 4, generally designated at 110 in FIG. 4A is a table showing four cycles of one presently preferred pseudo random algorithm generating a pseudo random white noise bit stream and generally designated at 120 in FIG. 4B is a graph of the bit stream output at each of the four cycles.

For one presently preferred and exemplary white noise sound, the bit rate is set to change the output bit at thirty-three (33) kHz producing sound at a maximum frequency of sixteen and a half (16.5) kHz. A sound wave is one up cycle and one down cycle so the period is twice the bit rate (or half the frequency). This means that the sound contains white noise from zero (0) kHz up to a maximum of sixteen and a half (16.5) kHz.

The initial values of Seed "1," Seed "2," Seed "3" and the Divisor are set as shown in table 110.

Cycle "1":
  Seed "1" is shifted left. The "0" in the leftmost bit of Seed "1" is placed in the CARRY register due to the shift. A "0" is shifted into the rightmost bit of Seed "1" from the CARRY register (this is the initial value of the CARRY register when starting the algorithm).
  Seed "2" is shifted left. The "0" from the CARRY register (originally in the leftmost bit of Seed "1") is shifted into the rightmost bit of Seed "2." The "1" from the leftmost bit of Seed "2" is shifted into the CARRY register.
  Seed "3" is shifted left. The "1" from the CARRY register (originally in the leftmost bit of Seed "2") is shifted into the rightmost bit of Seed "3." The "0" from the leftmost bit of Seed "3" is shifted into the CARRY register.
  The CARRY bit is tested. (If it is "1," then XOR Seed "1" and the Divisor. If it is "0," skip the XOR).
  Since the CARRY bit is "1," XOR Seed 1 and Divisor. The result is stored in variable Seed "1"—ie the Seed "1" register is replaced with the result of the XOR. This is one step, the XOR changes the value of Seed "1."
  The CARRY bit is tested and the output pin is set to correspond to the value. If CARRY is "1," the output pin is set to "1" (on/five (5) Volts). If CARRY is "0," the output pin is set to "0" (off/zero (0) Volts).
  The algorithm goes back to the start.

Cycle "2":
  Seed "1" is shifted left.
  Seed "2" is shifted left.
  Seed "3" is shifted left.
  The CARRY bit is tested.
  The XOR is skipped since the CARRY bit is "0."
  The CARRY bit is tested and the output pin is set to correspond to the value.
  The algorithm goes back to the start.

Cycle "3":
  Seed "1" is shifted left.
  Seed "2" is shifted left.
  Seed "3" is shifted left.
  The CARRY bit is tested.
  A XOR is performed on Seed "1" using the divisor since the CARRY bit is "1."
  The CARRY bit is tested and the output pin is set to correspond to the value.
  The algorithm goes back to the start.

Cycle "4":
  Seed "1" is shifted left.
  Seed "2" is shifted left.
  Seed "3" is shifted left.
  The CARRY bit is tested.
  A XOR is performed on Seed "1" using the divisor since the CARRY bit is "1."
  The CARRY bit is tested and the output pin is set to correspond to the value.

It will be appreciated that the pseudo random white noise generation algorithm disclosed herein is exemplary and that other pseudo random white noise generation algorithms could be employed without departing from the inventive concepts.

Figure 5:
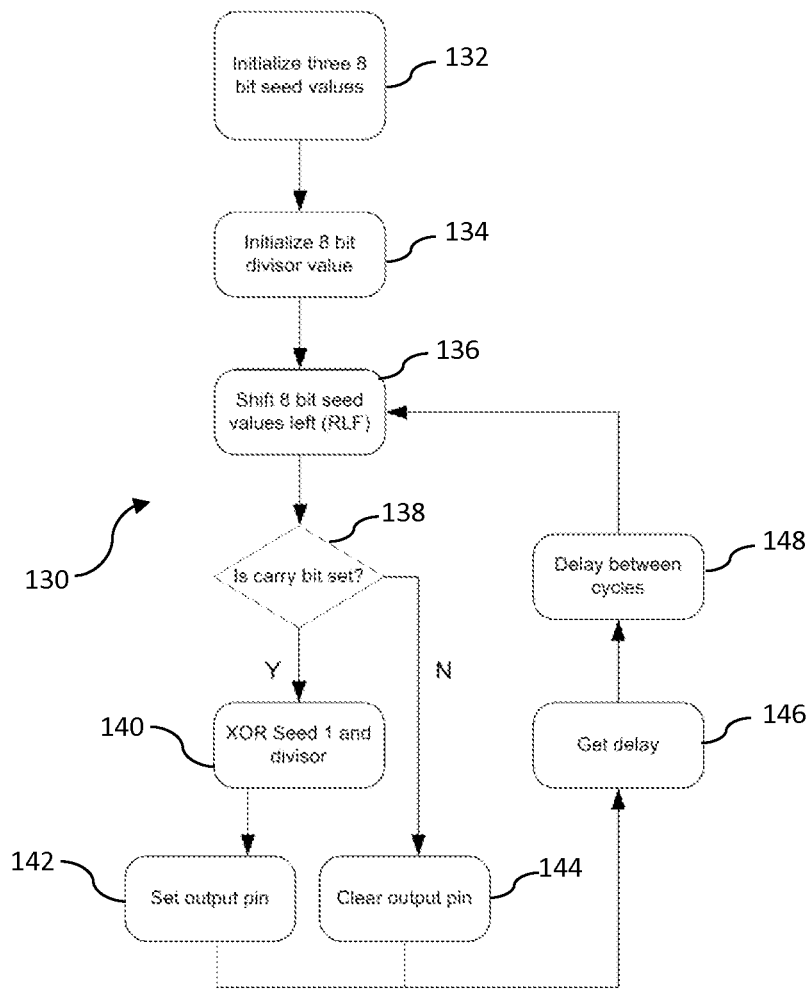
FIG. 5 is a flowchart illustrating the manner the processor of the pseudo random white noise generator algorithmically varies the bit rate of the pseudo random bit stream to controllably provide white noise tone control.

Referring now to FIG. 5, generally designated at 130 is a flowchart illustrating the manner the processor of the pseudo random white noise generator algorithmically varies the bit rate of the pseudo random bit stream to controllably provide white noise texture/tone control.

Processing as shown by the blocks 132-144 is the same as processing steps 92-104 (FIG. 3) and is not separately described herein for the sake of brevity of explication.

As shown by the block 146, the processor is operative after processing in the steps 142, 144 to get the delay input by the user to control the tone/texture of the white noise, and to introduce a delay between cycles as shown by the block 148. Processing then returns to the block 136.

As will be appreciated, the delay filters out higher frequencies with the result that the tone/texture of the white noise generated has lower pitch with increasing delay. Increasing the delay also increases the duration of each bit in the bit stream. This also changes the tone/texture of the sound.

Example of Tone/Texture Control

In one presently preferred and exemplary embodiment, the above-described algorithm generates bits at a maximum frequency of two hundred (200) kHz. The algorithm is ten (10) steps or five (5) microseconds per cycle. A twenty-five (25) microsecond delay on top of this clips the high frequencies. The result is a thirty (30) microsecond minimum time to change a bit or thirty-three (33) kHz bit frequency.

To change the tone and texture of the sound, the delay length is increased by fifteen (15) microseconds for each of ten (10) steps in response to user tone/texture control input. With the exemplary ten (10) different sounds available, the maximum delay is one hundred and sixty-five (165) microseconds leading to a loop of one hundred and seventy (170) microseconds. The sound output is white noise with a frequency from zero (0) kHz up to a maximum of two and nine tenths (2.9) kHz.

Figure 6:
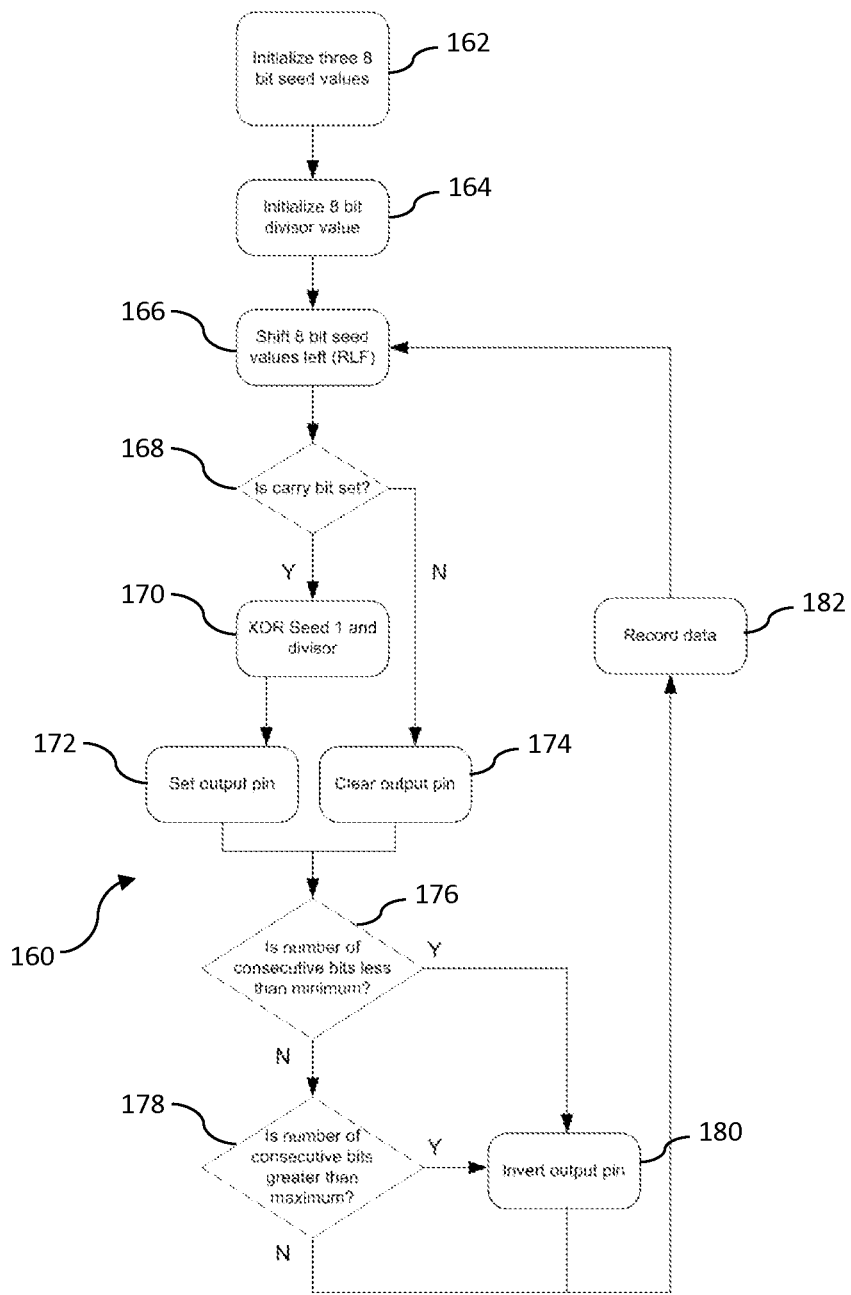
FIG. 6 is a flowchart illustrating the manner the processor of the pseudo random white noise generator algorithmically changes the sequence of the "1's" and "0's" of the pseudo random bit stream to controllably provide white noise bandwidth control.

Referring now to FIG. 6, generally designated at 160 is a flowchart illustrating the manner the processor of the pseudo random white noise generator algorithmically changes the sequence of the "1's" and "0's" of the pseudo random bit stream to controllably provide white noise bandwidth control.

Processing as shown by the blocks 162-174 is the same as processing steps 92-104 (FIG. 3) and is not separately described herein for the sake of brevity of explication.

As shown by the block 176, the processor is operative after processing in the steps 172, 174 to determine if the number of consecutive bits is less than the minimum. If not, as shown by block 178, the processor is operative to determine if the number of consecutive bits is greater than the maximum. If not, data is recorded, as shown by block 182, and processing returns to step 166. But if the number of consecutive bits is less than or more than the minimum, the output is inverted as shown by block 180, data is recorded as shown by block 182, and processing returns to the step 166.

Example of Bandpass Control

The band pass filter operates to ensure that the desired maximum and minimum frequencies are met. This is accomplished by ensuring that at least a given number of bits pass without a change (limit the upper frequency) while also ensuring that the number of consecutive unchanged bits is also limited (limit the lower frequency).

To accomplish this, the algorithm maintains a history (record) of the previous bits to enable comparison to the next generated bit. For the exemplary and presently preferred embodiment, having a delay added to yield a cycle time of fifty (50) microseconds, a minimum frequency of one (1) kHz is achieved by ensuring that the output bit changes at least once every ten (10) bits. If a maximum frequency of five (5) kHz is desired, the algorithm ensures that at least two (2) consecutive bits are the same.

The algorithm in this example monitors the bit stream generated by the white noise algorithm and applies the following rules.

If there are ten "1's" in a row, change the bit to a "0."
If there are ten "0's" in a row, change the bit to a "1."
If there are less than two "1's" in a row, change the bit to a "0."
If there are less than two "0's" in a row, change the bit to a "1."
If these conditions are not met, the bit is not changed.

Example of Peak Frequency Control

For white noise sound therapy, a peak can be defined as a band pass filter with a bandwidth of three (3) kHz or less. Of course a different definition of a peak frequency could be employed.

The band pass filter described hereinabove operates to deliver a peak frequency by ensuring that desired maximum and minimum frequencies are met. This is accomplished by ensuring that at least a given number of bits pass without a change (limits the upper frequency) while also ensuring that the number of consecutive unchanged bits is also limited (limiting the lower frequency).

To accomplish this, the algorithm maintains a history of the previous bits to enable comparison to the next generated bit. For the exemplary and presently preferred embodiment with a delay added to yield a cycle time of twenty-five (25) microseconds, a peak frequency of five (5) kHz is achieved by ensuring that the maximum frequency is six and a half (6.5) kHz and the minimum frequency is three and one half (3.5) kHz. This is achieved by ensuring that the output bit changes at least once every six (6) bits while ensuring that at least three (3) consecutive bits are the same.

Multiple peaks could be obtained by using two filters at once and applying the result to a second output pin. Each filter receives the same pseudo random white noise input and applies a different filter to the data to control two output pins to obtain two different outputs.

For multiple peaks, two filters controlling two separate output pins, not shown, could be used. Both filters accept the same input from the white noise bit stream and the results of the filters do not affect the bit stream itself. The two resultant bit streams may be combined on the audio amplification side without departing from the inventive concepts.

Many modifications of the present invention within the scope and spirit of the appended claims will become apparent to those of skill in the art without departing from the inventive concepts.

What is claimed is:

1. A sound machine providing white noise sound therapy for tinnitus sufferers and others seeking noise-masking or help to relax or to fall asleep, comprising:
a housing;
a user input interface mounted to said housing;
a pseudo random white noise generator mounted in said housing including a processor having an input port and an output port, said input port of said processor of said pseudo random white noise generator is coupled to the user interface, said processor of said pseudo random white noise generator is operative in response to a user input received at said user input interface to execute a pseudo-random number generation algorithm to generate in real-time a pseudo random digital bit stream of "1's" and "0's" at said output port at a bit rate that corresponds to sounds at frequencies audible to said tinnitus sufferers and said others seeking noise-masking or help to relax and fall asleep that range from a sound at a maximum frequency that is one-half said bit rate to sounds at frequencies less than said maximum frequency in dependence on said pseudo random digital bit stream that is generated in real-time;
an analog amplifier coupled to said output port of said processor of said pseudo random white noise generator operative in response to the pseudo random digital bit stream of "1's" and "0's" at said bit rate to provide an analog white noise signal having audible frequencies that range from said maximum frequency that is one-half said bit rate to said frequencies less than said maximum frequency that are audible to said tinnitus sufferers and others seeking noise-masking or help to relax and fall asleep; and
a speaker coupled to said analog amplifier responsive to the analog white noise signal to provide said white noise sound therapy for tinnitus sufferers and others seeking noise-masking or help to relax or to fall asleep.

2. The sound machine of claim 1, wherein the user input interface is a tone/texture user input interface, wherein the processor of the pseudo random white noise generator is operative to controllably change the bit rate of the pseudo random bit stream and thereby a tone/texture of the analog signal in response to a user tone/texture control input; wherein the tone/texture user input interface specifies a delay; wherein said pseudo random white noise generator cyclically produces each bit of said pseudo random digital bit stream of "1's" and "0's" at said bit rate for each of said cycles; and wherein said processor of said pseudo random white noise generator interposes said delay between each said cycle to controllably lower said bit rate and thereby controllably change the tone/texture of said analog white noise signal in response to user input tone/texture delay selection.

3. The sound machine of claim 1, wherein the user input interface is a frequency band user input interface, wherein the "1's" and "0's" of the pseudo random bit stream are a sequence of "1's" and "0's" and; wherein the processor of the pseudo random white noise generator is operative to controllably change the sequence of the "1's" and "0's" of the pseudo random bit stream and thereby the frequency band of the analog signal in response to a user frequency band control input; wherein said frequency band user input interface specifies minimum and maximum frequencies in said range from said sound at said maximum frequency that is one-half said bit rate to said sounds at frequencies less than said maximum frequency; wherein the pseudo random white noise generator cyclically produces each bit of said pseudo random digital bit stream of "1's" and "0's" for each of said cycles; wherein the processor of said pseudo random white noise generator is cyclically operative to maintain a record of said sequence of "1's" and "0's" for each of said cycles that have been actually generated in real time during each of said cycle; and wherein said processor is cyclically operative to examine said record to determine how many unchanged consecutive bits there are and to compare the number of unchanged consecutive bits in said record to rules that specify the minimum and maximum number of unchanged bits permitted that correspond to each said minimum and maximum frequency selected and cyclically changes the pseudo random bit said processor would otherwise have generated if needed to satisfy the required number of consecutive unchanged bits specified by said rules for each of said cycles.

4. The sound machine of claim 3, wherein the frequency band is a comparatively-wide bandpass frequency band defined by said minimum and maximum frequencies of therapeutic benefit to a particular user in accord with the minimum and maximum frequencies specified.

5. The sound machine of claim 3, wherein the difference between said minimum and maximum frequencies defines the frequency band, wherein the frequency band is a comparatively-narrow peak frequency band of therapeutic benefit to a particular user in accord with the comparatively-narrow peak frequency band specified.

6. A sound machine providing white noise sound therapy for tinnitus sufferers and others seeking noise-masking or help to relax or to fall asleep, comprising:
a housing;
a user input interface mounted to said housing;
a pseudo random white noise generator mounted in said housing including a processor having an input port and an output port, said input port of said processor of said pseudo random white noise generator is coupled to the user interface, said processor of said pseudo random white noise generator is operative in response to a user input received at said user input interface to execute a pseudo-random number generation algorithm to generate in real-time a pseudo random digital bit stream of "1's" and "0's" at said output port at a bit rate that corresponds to sounds at frequencies audible to said tinnitus sufferers and said others seeking noise-masking or help to relax and fall asleep that range from a sound at a maximum frequency that is one-half said bit rate to sounds at frequencies less than said maximum frequency; and
a speaker coupled to said pseudo random white noise generator and operative in response to the pseudo random digital bit stream of "1's" and "0's" to provide said white noise sound therapy for tinnitus sufferers and others seeking noise-masking or help to relax or to fall asleep having audible frequencies that range from said maximum frequency that is one-half said bit rate to said frequencies less than said maximum frequency that are audible to said tinnitus sufferers and others seeking noise-masking or help to relax and fall asleep.

* * * * *